(12) United States Patent
Dalla Pria et al.

(10) Patent No.: US 10,687,825 B2
(45) Date of Patent: Jun. 23, 2020

(54) DEVICE FOR THE RESECTION OF THE FEMUR

(71) Applicant: LIMACORPORATE S.P.A., San Daniele del Friuli (IT)

(72) Inventors: Paolo Dalla Pria, Udine (IT); Marco Dosso, Udine (IT); Fausto Sbaiz, Codroipo (IT)

(73) Assignee: LIMACORPORATE S.P.A., San Daniele del Friuli (IT)

( * ) Notice: Subject to any disclaimer, the term of this patent is extended or adjusted under 35 U.S.C. 154(b) by 569 days.

(21) Appl. No.: 15/510,333

(22) PCT Filed: Sep. 11, 2015

(86) PCT No.: PCT/IB2015/056976
§ 371 (c)(1),
(2) Date: Mar. 10, 2017

(87) PCT Pub. No.: WO2016/038575
PCT Pub. Date: Mar. 17, 2016

(65) Prior Publication Data
US 2017/0252047 A1   Sep. 7, 2017

(30) Foreign Application Priority Data

Sep. 11, 2014 (IT) .............................. UD2014A0149

(51) Int. Cl.
*A61B 17/15* (2006.01)
*A61B 90/00* (2016.01)
(Continued)

(52) U.S. Cl.
CPC .......... *A61B 17/151* (2013.01); *A61B 17/175* (2013.01); *A61B 90/06* (2016.02);
(Continued)

(58) Field of Classification Search
CPC ..... A61B 17/15; A61B 17/151; A61B 17/152; A61B 17/154; A61B 17/155; A61B 17/157; A61B 17/158; A61B 17/175; A61B 90/06
(Continued)

(56) References Cited

U.S. PATENT DOCUMENTS 8,545,508 B2   10/2013  Collazo
10,251,652 B2 *  4/2019  Budhabhatti ........ A61B 17/155
(Continued)

FOREIGN PATENT DOCUMENTS

DE   102007053058 B3   4/2009
EP       2581049 A1    4/2013
JP     2005000526 A    1/2005

OTHER PUBLICATIONS

Int'l Search Report and Written Opinion dated Dec. 23, 2015 in Int'l Application No. PCT/IB2015/056976.

*Primary Examiner* — Si Ming Ku
(74) *Attorney, Agent, or Firm* — Panitch Schwarze Belisario & Nadel LLP

(57) ABSTRACT

A device for resecting a femur includes a resection body provided with resection grooves configured to receive a cutting surgical instrument to obtain at least two sections of the femur. The resection body has two separate elements, selectively assembleable to each other in a stable and releasable manner. A first element is a cutting template, having the resection grooves. A second element is a measuring and reference member, having a plurality of measuring and reference holes configured to determine an angular offsetting with respect to a longitudinal axis of the femur, and an axial translation along the longitudinal axis of the femur between the two sections. A releasable holder is provided between the cutting template and the measuring and reference member. The measuring and reference holes
(Continued)

are made on the measuring and reference member according to a matrix associated with axial and angular coordinates in ordered rows and columns.

14 Claims, 3 Drawing Sheets

(51) Int. Cl.
    *A61B 17/17*     (2006.01)
    *A61B 17/00*     (2006.01)

(52) U.S. Cl.
    CPC ............ *A61B 2017/00477* (2013.01); *A61B 2090/061* (2016.02)

(58) Field of Classification Search
    USPC .................................................. 606/89, 102
    See application file for complete search history.

(56) References Cited

U.S. PATENT DOCUMENTS

| | | | |
|---|---|---|---|
| 2010/0087829 A1* | 4/2010 | Metzger | A61B 17/15 606/96 |
| 2011/0015636 A1 | 1/2011 | Katrana et al. | |
| 2011/0172672 A1* | 7/2011 | Dubeau | A61B 17/151 606/87 |
| 2013/0165936 A1 | 6/2013 | Myers | |
| 2013/0204257 A1* | 8/2013 | Zajac | A61B 17/155 606/87 |
| 2016/0106409 A1* | 4/2016 | Moholkar | A61B 17/025 606/90 |

\* cited by examiner

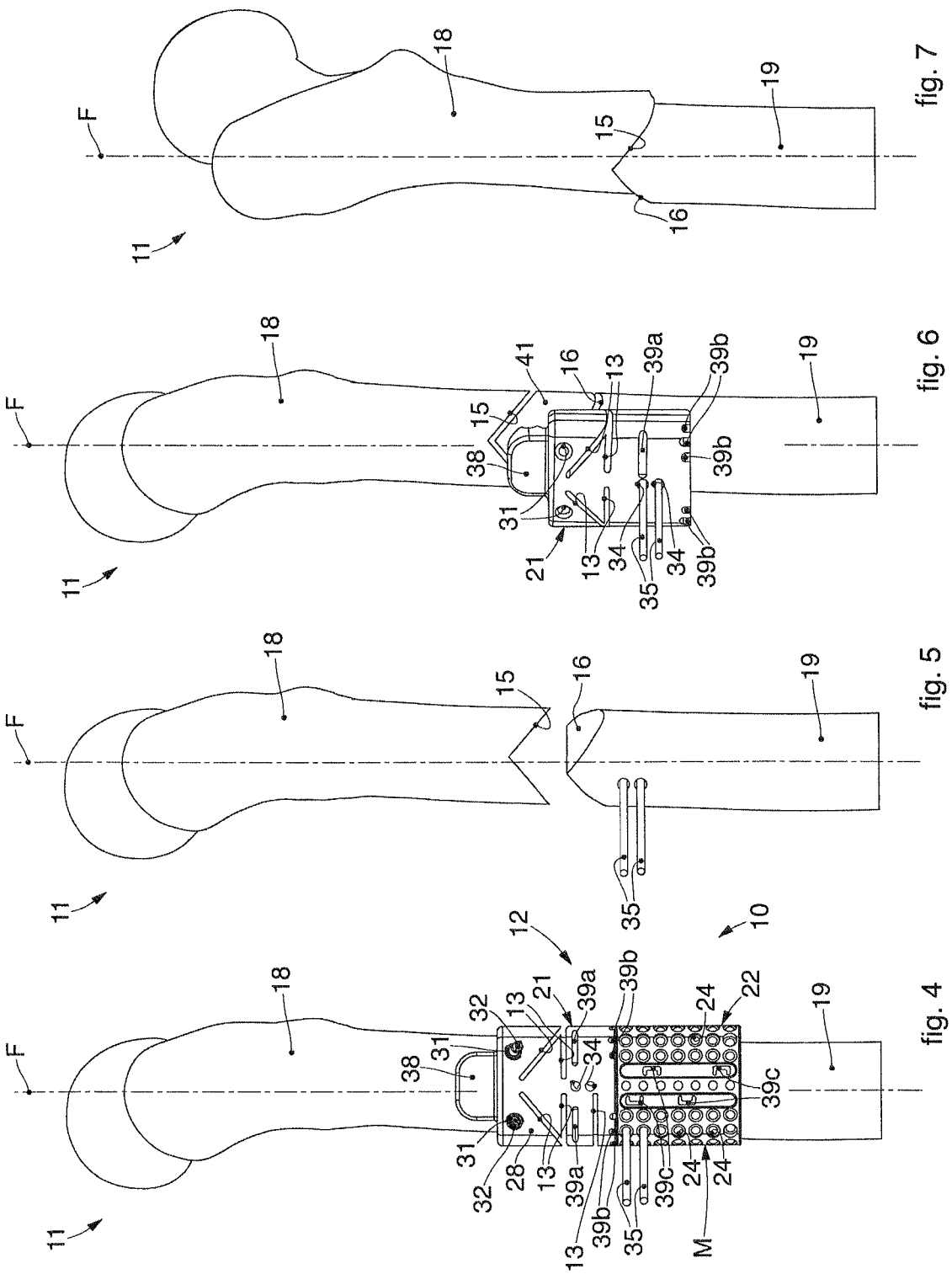

DEVICE FOR THE RESECTION OF THE FEMUR

CROSS-REFERENCE TO RELATED APPLICATION

This application is a Section 371 of International Application No. PCT/IB2015/056976, filed Sep. 11, 2015, which was published in the English language on Mar. 17, 2016, under International Publication No. WO 2016/038575 A1, the disclosure of which is incorporated herein by reference.

FIELD OF THE INVENTION

The present invention concerns a device for the resection of the human or animal femur, usable in orthopedic surgery operations, in particular minimally invasive prosthetic surgery, in the treatment of pathologies relating to the hip joint, in particular congenital or evolutionary dysplasia in man or in animals.

BACKGROUND OF THE INVENTION

Dysplasia of the hip is a known illness, widespread throughout the world, which consists of an articular deformity that starts during the inter-uterine life of the baby but continues to evolve during the first years of life, which makes it an evolutionary illness.

Dysplasia manifests itself in an excessive looseness of the joint, which leads the femoral head to exit from and return inside the acetabular cavity when subjected to external forces. If this instability is not diagnosed and treated, as the months pass the femoral head, subjected to the action of the muscles and then the body weight, gradually loses its relation with its natural seating, or paleocotyl, and rises upward, configuring a permanent dislocation of the hip and defining a new seating, or neocotyl.

If diagnosed in newborns, dysplasia can be cured almost completely using spreaders, redefining the position of the joint.

If the dysplasia is not treated in time in the newborn, it can develop and reach an arthritic stage.

Depending on the stage reached, and provided that the articular function has been retained, it is possible to intervene using corrective surgical operations, such as re-orientation osteotomies, typically prosthetic surgery interventions. These procedures respectively have the purpose of improving the relation between the articular heads, preventing or retarding the onset of arthrosis, and of increasing the cover of the femoral head, thus slowing down the progression of the illness.

These procedures consist in the resection of the femur at two points, in order to remove a portion thereof, normally from 1 to 4 cm in length, with the purpose of returning the head of the femur into the paleocotyl. From this osteotomy two bone stumps are produced, which are subsequently joined together again.

It is known to proceed using a flat osteotomy, in which the femur is sectioned with flat cuts. The disadvantage of this procedure is that, reconstructing the femur by rejoining the stumps sectioned by said flat cuts, the femur does not resist in the best possible way to the torsional stresses, and this can lead to a fracture or pseudo-arthrosis.

To overcome the disadvantages of flat osteotomy, it is known to operate using other variant types of osteotomy, such as for example V-shaped (chevron or double-chevron osteotomy), oblique or Z-shaped, which allow torsional stability of the joint. In fact, a V-shaped, oblique or Z-shaped cut of the femur allows a recoupling of the stumps that is resistant to torsional stresses.

It is known, during V-shaped, oblique or Z-shaped osteotomies, to use devices for the resection of the femur, applied to the femur itself using pins and/or Kirschner wires, with the purpose of defining a clean cut and of measuring the quantity of femur to be cut with the greatest accuracy. One example is described in the patent application JP-A-2005000526.

Known devices for the resection of the femur generally have a main resection body, parallelepiped shaped, suitable to rest on the femur.

The main resection body is a single piece, which has a plurality of resection grooves, mating in shape with the cut to be made, V-shaped for example, which function as a guide template for the cutting operation.

The resection grooves are suitably distanced from each other along the development of the femur so that the correct and desired portion can be removed, using only different and distanced resection grooves.

One disadvantage of known devices for the resection of the femur is that the profile of the cut made on the bone stumps does not allow them to rotate with respect to each other, that is, it allows them to be rejoined only if the profiles are flat and parallel, which condition occurs by not rotating the stumps. In particular, if the femur has an axial development with a certain torsional deformation, the rejoining of the stumps is imprecise and not effective.

This disadvantage occurs since very often subjects affected by dysplasia generally have a very pronounced anteversion of the neck of the femur, which is manifested with a great torsional deformation. In healthy subjects, the line of the neck is oriented forward by about 8-13°, while in subjects affected by dysplasia this value can go as high as 30° for example.

During the surgical osteotomy operation for treating dysplasia, it is therefore also usual to restore the anatomic anteversion of the femur by reciprocal mobilization of the stumps, that is, by rotating them with respect to each other, in order to orient the femoral prosthesis with respect to the acetabular prosthesis in the best possible way.

It is therefore necessary to make the two stumps able to be coupled precisely in said reciprocally rotated position.

Document US 2011/0015636 A1 describes a resection guide for the joint of the humerus, which provides two degrees of freedom: rotation and translation, along the axis of articulation of the humerus. The purpose of the guide is substantially to make a seating in the joint of the humerus where a prosthesis can be positioned.

The resection guide described in US 2011/0015636 A1 therefore concerns a bone segment, that of the humerus, which is different from the bone segment of the femur. Moreover, the guide works along the axis of articulation of the humerus, which is substantially parallel to the transverse anatomical plane of the human body and orthogonal to the longitudinal axis of the femur, which is perpendicular to the transverse anatomical plane of the human body. The guide is therefore unsuitable and ineffective for a resection of the femur and in particular for a resection of the femur that allows to define the length of the femur to be removed and the angle between the stumps, and to couple them precisely so that it is possible to intervene effectively in order to restore, in particular, the anatomical anteversion.

There is therefore a need to perfect a device for the resection of the femur, usable in orthopedic surgery operations, in particular minimally invasive prosthetic surgery, which can overcome at least one of the disadvantages of the state of the art.

In particular, one purpose of the present invention is to obtain a device for the resection of the femur that can be used in all types of osteotomy interventions.

Another purpose of the present invention is to obtain a device for the resection of the femur that allows to define the length of the femur to be removed and the angle between the stumps, so that they can be coupled precisely and so that it is possible to intervene effectively in order to restore the anatomical anteversion.

Another purpose is to obtain a device for the resection of the femur that is easy to use.

Another purpose of the present invention is to obtain a device for the resection of the femur that works substantially along the longitudinal axis of the femur.

Another purpose of the present invention is to obtain a device that can be used effectively also in the correction of the abnormal angulation of the proximal femur.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purposes, the present invention concerns a device for the resection of the femur, usable in orthopedic surgery operations, in particular minimally invasive prosthetic surgery. In some forms of embodiment, the device for the resection of the femur comprises a resection body provided with resection grooves configured to receive a cutting surgical instrument to obtain at least two sections of the femur.

According to one aspect of the present invention, the resection body consists of two separate elements, able to be selectively assembled to each other in a stable and releasable manner, of which a first element is a cutting template provided with the resection grooves. The second element is a measuring and reference member provided with a plurality of measuring and reference holes configured to determine an angular offsetting, with respect to the longitudinal axis of the femur, and an axial translation, along the longitudinal axis of the femur, between the two sections of the femur. Furthermore, releasable holding means are provided between the cutting template and the measuring and reference member. Moreover, the measuring and reference holes are made on the measuring and reference member according to a matrix associated with axial and angular coordinates in ordered rows and columns.

The presence of the releasable holding means allows to associate and dis-associate the cutting template and the measuring and reference member with/from each other, allowing to make the resection body assume a variable configuration.

According to one aspect of the present invention, the resection body is configured to assume an assembled first cutting condition, in which the cutting template is suitable to cooperate with surgical instruments to perform a first section and is associated in a single body with the measuring and reference member.

Furthermore, the resection body is configured to assume a dis-assembled second cutting condition, in which the cutting template is angularly offset and axially translated with respect to the assembled first cutting condition, and is suitable to cooperate with surgical instruments to obtain a second section, angularly offset and axially translated with respect to the first section.

The double condition in which the cutting template can be configured allows to make two sections, reciprocally offset and angled, which allow to restore the anteversion of the femur. The two sections can be obtained using a single device according to the present invention and can be made in succession to each other, in a short time.

Moreover, the presence of multiple measuring and reference holes allows to define the two sections with great precision.

In fact, the choice of holes allows to identify cutting coordinates that indicate by how much the second section is angularly offset and axially translated with respect to the first section.

These and other aspects, characteristics and advantages of the present disclosure will be better understood with reference to the following description, drawings and attached claims. The drawings, which are integrated and form part of the present description, show some forms of embodiment of the present invention, and together with the description, are intended to describe the principles of the disclosure.

The various aspects and characteristics described in the present description can be applied individually where possible. These individual aspects, for example aspects and characteristics described in the attached dependent claims, can be the object of divisional applications.

It is understood that any aspect or characteristic that is discovered, during the patenting process, to be already known, shall not be claimed and shall be the object of a disclaimer.

BRIEF DESCRIPTION OF THE DRAWINGS

These and other characteristics of the present invention will become apparent from the following description of some forms of embodiment, given as a non-restrictive example with reference to the attached drawings wherein:

FIGS. 4-7 are front views of operating steps of the device in FIG. 1;

Figure 1:
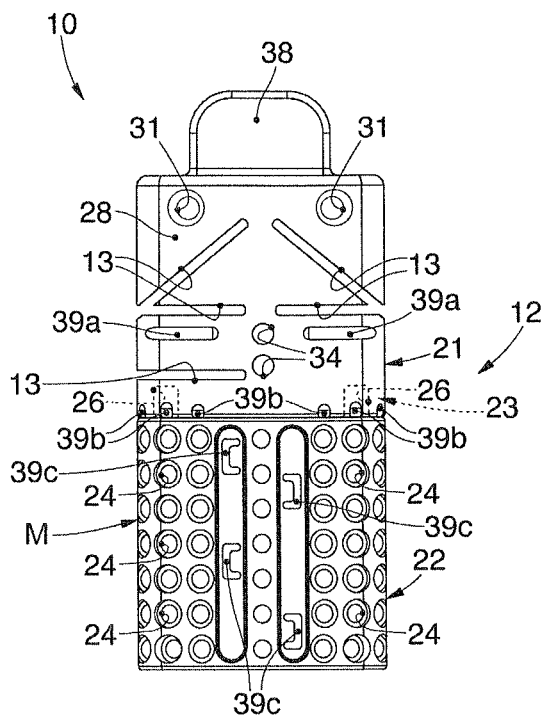
FIG. 1 is a front view of the device for the resection of the femur according to the present invention.

To facilitate comprehension, the same reference numbers have been used, where possible, to identify identical common elements in the drawings. It is understood that elements and characteristics of one form of embodiment can conveniently be incorporated into other forms of embodiment without further clarifications.

DETAILED DESCRIPTION OF SOME FORMS OF EMBODIMENT

We shall now refer in detail to the various forms of embodiment of the present invention, of which one or more examples are shown in the attached drawings. Each example is supplied by way of illustration of the invention and shall not be understood as a limitation thereof. For example, the characteristics shown or described insomuch as they are part of one form of embodiment can be adopted on, or in association with, other forms of embodiment to produce another form of embodiment. It is understood that the present invention shall include all such modifications and variants.

FIGS. 1-7 are used to describe forms of embodiment of a device 10 for the resection of the femur 11 according to the present description, usable in orthopedic surgery operations, in particular minimally invasive prosthetic surgery, and also usable in operations to correct the abnormal angulation of the proximal femur. The femur 11 has a longitudinal axis F, see FIGS. 4-8.

In some forms of embodiment, the device 10 comprises a resection body 12 provided with one or more resection grooves 13 configured to receive a cutting surgical instrument. The resection grooves 13 are through, to allow the cutting surgical instrument to pass and to obtain at least two sections 15, 16 of the femur 11, in particular defining two complementary stumps 18, 19. For example, two, three, four or more resection grooves 13 can be provided, in pairs or single, symmetrical or not with respect to the center line. In possible forms of embodiment, described for example using FIGS. 1, 2, 4 and 6, resection grooves 13 can be provided with different angles of inclination, for example in order to obtain a resection with a different geometry (for example Z-shaped, oblique, V-shaped, chevron or double chevron shaped).

According to the present description, the resection body 12 consists of two separate elements 21, 22, able to be selectively assembled to each other in a stable and releasable manner, according to needs and the operating steps.

In particular, a first element of the resection body is a cutting template 21 provided with said resection grooves 13, while a second element is a measuring and reference member 22 provided with a plurality of measuring and reference holes 24 configured to determine an angular offsetting with respect to the longitudinal axis F of the femur 11 and an axial translation between the two sections 15, 16 of the femur 11. The axial translation is effected along the longitudinal axis F of the femur 11.

In particular, according to forms of embodiment described here, the resection body 12 can be configured to assume an assembled first cutting condition, in which the cutting template 21 and the measuring and reference member 22 can be associated with each other in a single body. In this condition the cutting template 21 can be attached to the femur 11 and can be suitable to cooperate with surgical cutting instruments to carry out a first section 15.

The resection body 12 can be configured to assume a dis-assembled, second cutting condition, in which the cutting template 21 is angularly offset and axially translated with respect to the assembled, first cutting condition, and is suitable to cooperate with surgical cutting instruments to obtain a second section 16 of the femur 11 angularly offset and axially translated with respect to the first section 15. In the second cutting condition, the cutting template 21 and the measuring and reference member 22 are separate from each other and dis-associated. In any case, the position of the cutting template 21 on the femur 11 in the second cutting condition is coordinated with the position of the measuring and reference member 22 in the assembled first cutting condition.

Figure 2:
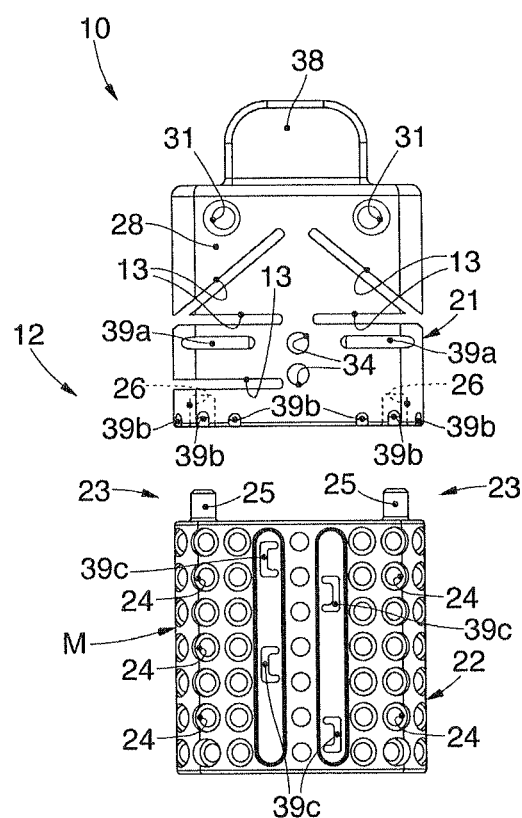
FIG. 2 is an exploded front view of the device in FIG. 1.

The cutting template 21 and the measuring and reference member 22 can be selectively coupled to define a single body, see FIG. 1 for example, or de-coupled to define two separate bodies, see FIG. 2 for example.

In some forms of embodiment, the cutting template 21 and the measuring and reference member 22 can be connected releasably by mechanical coupling, for example by snap-in coupling, same-shape or geometric coupling, coupling by interference, or by magnetic holding, or again a combination of the above.

In particular, according to the present description, releasable holding means 23 are provided between the cutting template 21 and the measuring and reference member 22.

The releasable holding means 23, which can be the mechanical or magnetic type, are configured to obtain the desired type of connection between the cutting template 21 and measuring and reference member 22 as discussed above.

In some forms of embodiment, the releasable holding means 23 can include connection pins 25 and mating apertures 26 to allow the coupling thereof. Advantageously, the connection pins 25 are magnetic connection pins and the apertures 26 include a ferromagnetic material, or at least one sensitive to a magnetic field, to obtain a magnetic holding effect in cooperation with the connection pins 25.

In particular, the cutting template 21 can include the connection pins 25 (male part of the connection) and the measuring and reference member 22 can be provided with the apertures 26 (female part of the connection). Or, vice versa, in some forms of embodiment, the connection between the cutting template 21 and the measuring and reference member 22 can be configured inversely, and the apertures 26 (female part of the connection) can be made on the cutting template 21 and the connection pins 25 (male part of the connection) can be made on the measuring and reference member 22.

In some forms of embodiment, described for example with reference to FIG. 1, the measuring and reference member 22 can be provided with the connection pins 25, while the cutting template 21 can be provided with the apertures 26.

The resection body 12 is suitable to receive attachment elements 35 to be attached directly on the femur 11 in the assembled and dis-assembled condition. The attachment elements 35 can be Kirschner wires for example, known in the surgical orthopedic fields, or pins or pegs for orthopedic use, inserted and guided for example by Kirschner wires.

The attachment elements 35 can be inserted into the femur 11 and kept fixed in position, both in the second cutting condition and in the first cutting condition of the device 10.

In some forms of embodiment, the measuring and reference member 22 can receive the attachment elements 35 to fix the first cutting condition of the device 10, which are inserted in particular into the corresponding measuring and reference holes 24.

Once coupled with the desired measuring and reference holes 24 of the measuring and reference member 22, the attachment elements 35 supply a correct and repeatable reference of the angular offsetting and the axial translation needed to complete the osteotomy and to restore the anatomical anteversion.

In fact, when the cutting template 21 is put in its second cutting condition, it is centered and guided in the correct angular and axial position cooperating with the attachment elements 35, in particular by its own attachment and reference holes 34, described in more detail hereafter.

Advantageously, the measuring and reference holes 24 can be made with a regular geometry on the measuring and reference member 22 according to a matrix M associated with axial and angular coordinates in orderly lines and columns, where groups of measuring and reference holes 24 that develop along the lines indicate different values of angular position, both toward the right and toward the left, whereas groups of measuring and reference holes 24 that develop along the columns indicate different values of axial position.

In particular, it will be possible to identify, in said matrix M, a central group of measuring and reference holes 24 that vary only the axial position along the axis of the femur 11, and two lateral groups of measuring and reference holes that allow to vary the angular position around the longitudinal axis F of the femur 11, in one direction or the other. Clearly, the groups can be combined in various ways so as to vary both the axial position and the angular position of the two sections 15 and 16.

To orient univocally the cutting template 21 in the second cutting condition, it is necessary however to identify two coordinates. The cutting template 21, in fact, is suitable to be associated in the second cutting condition with the femur 11 by the attachment elements 35 fixed in the coordinates chosen by means of the measuring and reference holes 24.

In some forms of embodiment, which can be combined with all the forms of embodiment described here, the lines in twos can indicate the same axial translation, so that two different coordinates that render the second cutting condition of the cutting template 21 univocal are also associated with the same axial translation.

For this reason, the measuring and reference member 22 can also be provided with indicators 39c able to indicate which lines define the same axial translation and therefore allow to make the second section 16 at the desired distance from the first section 15, and at the same time render its position univocal. The indicators 39c can be the visual or tactile type or a combination thereof. For example, the indicators 39c can be incisions, cavities, recesses, notches or similar bas-relief elements.

Figure 3:
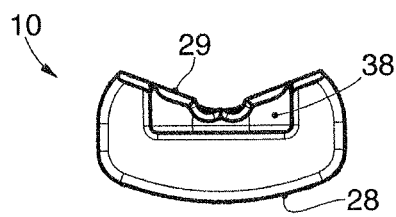
FIG. 3 is a plan view of the device in FIG. 1.

The cutting template 21 can be provided with a first surface 28, facing externally during use, and a second surface 29, in contact with the femur 11 during use, see FIG. 3 for example.

The second surface 29 can be suitably shaped to adapt to the conformation of the femur 11 and define a stable support for the device 10.

The cutting template 21 can be made in a single body on which the resection grooves 13 are made through.

The resection grooves 13 can be suitable to interact with surgical instruments, such as for example cutters, driven manually or robotized, which define the sections 15, 16 of the femur 11 and guide the cutting thereof.

The resection grooves 13 can have a shape compatible with the type of osteotomy to be made.

In forms of embodiment described with reference to FIGS. 1-7, the resection grooves 13 comprise two cutting profiles, reciprocally linear and symmetrically inclined to define a V-shaped section (chevron or double chevron).

In other forms of embodiment, the resection grooves 13 comprise a cutting profile to define a Z-shaped section, or again an oblique or flat section.

The cutting template 21 can comprise safety holes 31, through in the body of the cutting template 21, suitable to receive removable safety elements 32.

In particular, the coupling of the safety holes 31 and safety elements 32 with the femur 11 is suitable to stabilize the first cutting condition of the device 10 on the femur 11.

In some forms of embodiment, which can be combined with all the forms of embodiment described here, the safety elements 32 can be Kirschner wires, or pins or pegs guided by Kirschner wires.

As mentioned briefly above, the cutting template 21 can also comprise said attachment and reference holes 34, through, and suitable to receive the attachment elements 35.

The coupling of the attachment and reference holes 34 and attachment elements 35 allows to constrain the second cutting condition of the cutting template 21.

In some forms of embodiment, the attachment and reference holes 34 can be present in the same number as the attachment elements 35 used.

With reference for example to FIGS. 1-7, the attachment and reference holes 34 can be at least two in number.

The attachment and reference holes 34 can be aligned with each other along the extension of the femur 11, in particular aligned vertically.

In some forms of embodiment, which can be combined with all the forms of embodiment described here, the cutting template 21 can also comprise indicators 39a, 39b configured to guide it in reaching the second cutting condition.

The indicators 39a, 39b can be made on the first surface 28 to allow them to be read easily. For example, the cutting template 21 can have right/left indicators 39a and position/angular rotation indicators 39b. The indicators 39a, 39b can also be incisions, cavities, recesses, notches or similar bas-relief elements.

The cutting template 21 also comprises an assembly plate 38 protruding from the first surface 28 of the cutting template 21 along the development of the femur 11. The assembly plate 38 can be suitable to stabilize the position of the cutting template 21 on the femur 11.

For the purposes of clarity, we shall now describe a possible procedure for using the device 10 according to forms of embodiment described here.

First of all, the resection body 12 is configured in the first cutting condition, that is, where the cutting template 21 is associated with the measuring and reference member 22 by the releasable holding means 23.

Subsequently, the device 10 with the resection body 12 configured in this way is disposed so that the second surface 29 is resting on the femur 11.

The current position of the resection grooves 13 made on the cutting template 21 with respect to the femur 11, accurately defined by the orthopedic surgeon, defines the position of the first section 15.

Before cutting the first section 15, the dis-assembled second cutting condition which the cutting template 21 has to assume is identified and defined, inserting two attachment elements 35 through the measuring and reference holes 24 so that they are fixed in the femur 11.

The choice of measuring and reference holes 24 depends on the position that the cutting template 21 is supposed to have in the second cutting condition.

Merely by way of example, with reference to FIG. 4, the two attachment elements 35 are positioned so that the second cutting condition is rotated with respect to the first, for example by 30° to the left, and is axially translated by 3 centimeters. It is clear that other angular rotation values and other translation values are possible, depending on operating requirements.

The attachment elements 35 will remain associated to the femur 11 until the end of the surgical procedure, to define a stable, reliable and precise reference. Moreover, the attachment elements 35 clamp and define the first cutting condition of the device 10.

As a precautionary measure, safety wires 32 can also be inserted inside respective safety holes 31 of the cutting template 21 and then fixed in the femur 11 to prevent accidental movements of the resection body 12 during cutting.

Subsequently, the first section 15 is made on the femur 11 using the resection grooves 13 present on the cutting template 21 as a guide, to thus define a first stump 18.

The resection body 12 is removed from the femur 11, detaching it from the attachment elements 35 and removing the safety wires 32, see FIG. 5 for example. The cutting template 21 is separated from the measuring and reference member 22, releasing the releasable holding means 23.

The cutting template 21 is again associated with the femur 11, inserting the attachment and reference holes 34 through the two attachment elements 35 that have remained inserted in the femur 11.

By way of example, the resection grooves 13 will now be offset for example by 30° to the left and at 3 centimeters with respect to the first section 15. In this condition it is enough to associate only the cutting template 21 to the femur 11, see FIG. 6 for example.

In the second cutting condition, the second section 16 is made on the femur 11, again using the resection grooves 13 of the cutting template 21 as a guide and defining the second stump 19.

Once the second section 16 has been made, the cutting template 21 is removed from the femur 11, detaching it from the attachment elements 35.

The attachment elements 35 and the safety elements 32 still fixed on the femur 11 are made safe using known techniques.

After having made the two sections 15, 16, the femur 11 is seen divided into two stumps 18, 19 and a bone portion 41 is removed, equivalent, with reference to FIGS. 4-7, to a length of 3 centimeters of femur 11 removed.

The two stumps 18, 19 have complementary sections 15, 16 only if, for example, the second stump 19 is rotated for example by 30° in order to couple with the first stump 18, thus restoring the correct alignment of the anatomical anteversion.

Figure 8:
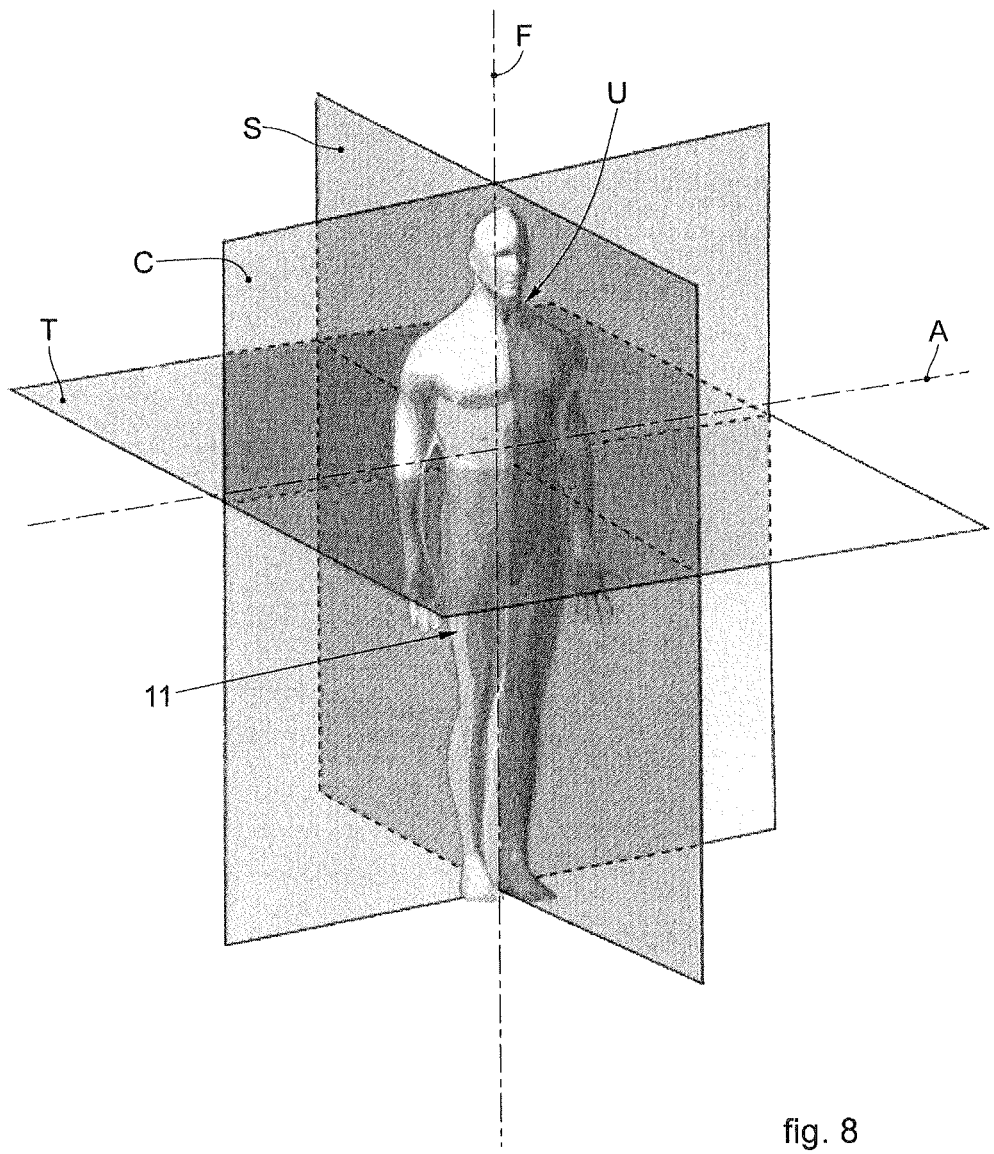
FIG. 8 is a schematic view of the human body in which the anatomical planes are identified.

FIG. 8 shows schematically a human body U in which three anatomical planes are identified: a sagittal anatomical plane S, a coronal anatomical plane C and a transverse anatomical plane T. The present device 10 operates effectively and advantageously along the longitudinal axis F of the femur 11, which is orthogonal to the transverse anatomical plane T. The transverse anatomical plane T is parallel to the axis A of articulation of the humerus, along which the guide described in US 2011/0015636 A1 described above operates.

By means of the present device 10 for the resection of the femur 11, which has two degrees of freedom and operates along the same longitudinal axis of the femur 11, it is possible to section the femur 11 effectively and precisely, and to reposition it axially and angularly, therefore effecting a reconditioning of the anatomy of the bone.

It is clear that modifications and/or additions of parts may be made to the device 10 for the resection of the femur, usable in orthopedic surgery operations, in particular minimally invasive prosthetic surgery, as described heretofore, without departing from the field and scope of the present invention.

It is also clear that, although the present invention has been described with reference to some specific examples, a person of skill in the art shall certainly be able to achieve many other equivalent forms of device for the resection of the femur, usable in orthopedic surgery operations, in particular minimally invasive prosthetic surgery, having the characteristics as set forth in the claims and hence all coming within the field of protection defined thereby.

The invention claimed is:

1. A device for resecting a femur, the device comprising:
   a resection body having a first element and a separate second element, the first and second elements being selectively assembleable to each other in a stable and releasable manner,
   the first element being a cutting template having at least one resection groove configured to receive a cutting surgical instrument to obtain at least two sections of the femur, and
   the second element being a measuring and reference member having a plurality of measuring and reference holes positioned thereon in ordered rows and columns according to a matrix associated with axial and angular coordinates, the holes being configured to determine an angular offset with respect to a longitudinal axis of the femur and an axial translation along the longitudinal axis of the femur between the at least two sections, and
   a releasable holder positioned between the cutting template and the measuring and reference member, for assembling the cutting template and the measuring and reference member together and releasing the cutting template and the measuring and reference member from one another,
   wherein groups of measuring and reference holes along the rows of the matrix indicate different values of angular position, both toward the right and toward the left, and groups of measuring and reference holes along the columns of the matrix indicate different values of axial position.

2. The device of claim 1, wherein the cutting template is suitable to cooperate with surgical instruments to carry out a first section and is associated in a single body to the measuring and reference member, in an assembled, first cutting condition of the resection body.

3. The device of claim 2, wherein, in a dis-assembled, second cutting condition of the resection body, the cutting template is angularly offset and axially translated relative to the assembled, first cutting condition, and is suitable to cooperate with surgical instruments to obtain a second section angularly offset and axially translated with respect to the first section.

4. The device of claim 3, wherein each of the measuring and reference holes correlates to a respective angular and axial coordinate, to define the second cutting condition.

5. The device of claim 4, wherein, in the first cutting condition, the measuring and reference holes are suitable to receive attachment elements corresponding with the angular and axial coordinates in order to define the second cutting condition of the cutting template.

6. The device of claim 5, wherein the cutting template further comprises attachment and reference holes for receiving the attachment elements in order to position the cutting template in the second cutting condition.

7. The device of claim 1, wherein the at least one resection groove comprises two linear cutting profiles reciprocally symmetrical and inclined to define V-shaped sections.

8. The device of claim 1, wherein the at least one resection groove comprises a cutting profile to define Z-shaped sections.

9. The device of claim 1, wherein the at least one resection groove comprises a cutting profile to define oblique sections.

10. The device of claim 1, wherein the at least one resection groove comprises a cutting profile to define flat sections.

11. The device of claim 1, wherein the releasable holder comprises connection pins and mating coupling apertures.

12. The device of claim 1, wherein the releasable holder is magnetic.

13. The device of claim 1, wherein the releasable holder is mechanical.

14. The device of claim 1, wherein the releasable holder is magnetic and mechanical.

* * * * *